United States Patent [19]

Bonifaz

[11] 4,393,265
[45] Jul. 12, 1983

[54] LIGHT MONOOLEFINS FROM METHANOL AND/OR DIMETHYL ETHER

[75] Inventor: Cristobal Bonifaz, Chadds Ford, Pa.

[73] Assignee: E. I. Du Pont de Nemours & Co., Wilmington, Del.

[21] Appl. No.: 286,604

[22] Filed: Jul. 24, 1981

[51] Int. Cl.$^3$ .................. C07C 1/24; C07C 1/20; B01J 29/38; B01J 29/06

[52] U.S. Cl. .................. 585/639; 252/416; 252/455.2; 585/640

[58] Field of Search .................. 585/640, 639

[56] References Cited

U.S. PATENT DOCUMENTS

| | | | |
|---|---|---|---|
| 3,257,310 | 6/1966 | Plank et al. | 252/455 Z |
| 3,407,148 | 10/1968 | Eatwood et al. | 252/420 |
| 3,428,550 | 2/1969 | Erickson et al. | 252/455 Z |
| 3,911,041 | 10/1975 | Kaeding et al. | 260/282 |
| 4,025,575 | 5/1977 | Chang et al. | 260/682 |
| 4,025,576 | 5/1977 | Chang et al. | 260/682 |
| 4,052,479 | 10/1977 | Chang et al. | 260/682 |
| 4,062,905 | 12/1977 | Chang et al. | 260/682 |
| 4,066,714 | 1/1978 | Rodewald | 260/682 |
| 4,079,095 | 3/1978 | Givens et al. | 260/682 |
| 4,079,096 | 3/1978 | Givens et al. | 260/682 |
| 4,083,888 | 4/1978 | Caesar et al. | 200/682 |
| 4,083,889 | 4/1978 | Caesar et al. | 260/682 |
| 4,148,835 | 4/1979 | Chen et al. | 260/682 |
| 4,172,856 | 10/1979 | Spencer et al. | 585/640 |
| 4,197,214 | 4/1980 | Chen et al. | 252/416 |
| 4,229,608 | 10/1980 | Chen et al. | 585/640 |
| 4,238,631 | 12/1980 | Daviduk et al. | 585/639 |
| 4,247,731 | 1/1981 | Wunder et al. | 585/640 |
| 4,296,266 | 10/1981 | Wunder et al. | 585/640 |

FOREIGN PATENT DOCUMENTS

| | | |
|---|---|---|
| 6501 | 9/1980 | European Pat. Off. . |
| 34444 | 8/1981 | European Pat. Off. . |
| 36704 | 9/1981 | European Pat. Off. . |

OTHER PUBLICATIONS

B. B. Singh et al., Chem. Eng. Comm., 4, 749 (1980).
W. W. Kaeding and S. A. Butter, J. Catalysis 61, 155 (1980).
R. G. Anthony and B. B. Singh, Chem. Eng. Comm. 6, 215 (1980).

*Primary Examiner*—P. E. Konopka

[57] ABSTRACT

Process of preparing light monoolefins by:

(a) activating a hydrogen-exchanged aluminosilicate catalyst having a silica to alumina ratio of less than 12 and, optionally, containing added metal cations, by treating with steam at a temperature of at least 400° C., preferably 450° to 520° C.;

(b) contacting the steam-activated catalyst in a reaction zone, at a temperature of about 350° to about 600° C., preferably 450° to 520° C., with a gas stream consisting essentially of dimethyl ether or a mixture of methanol and dimethyl ether, as reactant, and sufficient water such that the mole ratio of water to ether in the reaction zone is at least 0.3; at a pressure of about 0.2 to about 30 atmospheres (about 20 to about 3000 kPa), preferably atmospheric pressure (100 kPa), and at a weight hourly space velocity (WHSV) of greater than about 0.5 $h^{-1}$, preferably 1 to 150 $h^{-1}$, to convert at least 85 wt % of the reactant to hydrocarbons comprising at least 50 wt % ethylene and propylene, said 85% conversion being achieved before the contacting has exceeded 1 g of reactant per g of catalyst, preferably before exceeding 0.3 g of reactant per g of catalyst, more preferably before exceeding 0.1 g of reactant per g of catalyst until the catalyst is spent; and (c) regenerating the spent catalyst with a mixture comprising steam and oxygen at a temperature of at least 400° C., preferably 450° to 520° C.

15 Claims, No Drawings

LIGHT MONOOLEFINS FROM METHANOL AND/OR DIMETHYL ETHER

DESCRIPTION

Technical Field

This invention relates to the production of hydrocarbons rich in light monoolefins, particularly ethylene and propylene, from methanol and/or dimethyl ether using certain aluminosilicates.

Background

It is well known in the art that monoolefins containing 2 to 4 carbon atoms can be produced from methanol and/or dimethyl ether in the presence of both natural and synthetic zeolitic catalysts.

U.S. Pat. No. 4,062,905 discloses the formation of a hydrocarbon product, rich in ethylene and propylene, by contacting methanol and/or dimethyl ether with an air-calcined zeolite catalyst having pores which are less than 6 A (0.6 nm) in the major dimension. Operable catalysts include chabazite, erionite, zeolite T and zeolite ZK-5, preferably in the hydrogen form. Reaction conditions include an operating temperature of about 500° F. (260° C.) to about 1100° F. (593° C.), a pressure of about 0.2 to about 30 atmospheres (about 20 to about 3000 kPa), and a liquid hourly space velocity of about 0.1 to about 200. Also disclosed is the use of carrier gases or diluents, for example, helium, hydrogen or nitrogen. Patentees exemplify yields of 44 wt % ethylene and 33 wt % propylene at 5% conversion, and 46 wt % ethylene and 26 wt % propylene at 80% conversion. The catalyst is regenerated (de-carbonized) by heating in air.

U.S. Pat. No. 4,079,095 discloses the formation of light olefins by contacting methanol and/or dimethyl ether with an air-calcined zeolite of the erionite-offretite type. Reaction conditions include an operating temperature of about 500° F. (260° C.) to about 1000° F. (538° C.), a pressure of about 0.2 to about 30 atmospheres (about 20 to about 3000 kPa), and a weight hourly space velocity (WHSV), that is, g/h of reactants and additives charged/g of catalyst, of about 0.1 to about 30 $h^{-1}$; at least 0.25 mole of water per mole of organic reactant is added to lengthen the catalyst cycle life and to increase the selective production of ethylene and propylene. The zeolite catalyst is preferably employed in its hydrogen form. The catalyst is regenerated by heating in air. The related U.S. Pat. No. 4,079,096 discloses a similar process using ZSM-34, a crystalline aluminosilicate zeolite of the erionite-offretite type, as the catalyst.

U.S. Pat. No. 4,247,731 discloses the formation of lower alkenes from methanol and/or dimethyl ether at a temperature of 300° to 500° C., optionally in the presence of a diluent such as nitrogen, carbon dioxide, alkenes or water, at an elevated or reduced pressure, over an air-calcined aluminum silicate catalyst, including chabazites, erionites and mordenites, which contains 0.1 to 10 wt % manganese and, optionally, another metal, for example, magnesium, as a co-catalyst. The catalyst is regenerated under relatively mild conditions by burning off coke deposits with air or oxygen and steam. A hydrocarbon product containing 46.9% ethylene and 29.2% propylene is exemplified.

U.S. Pat. No. 4,229,608 discloses a cyclic process for converting methanol and/or dimethyl ether to hydrocarbons, rich in ethylene and propylene, using an air-calcined fluidized small-pore zeolite such as chabazite or erionite as catalyst, a temperature of about 800° to about 1150° F. (about 430° to about 620° C.), a residence time of less than 30 seconds, preferably less than 15 seconds; the catalyst is separately regenerated in air at 1200° to 1400° F. (650° to 760° C.).

Singh et al., Chem. Eng. Comm. 4, 749 (1980), report on work on the tubular reactor system and disclose that the most promising catalyst for the conversion of methanol to olefins is chabazite ion-exchanged with ammonia and a rare earth chloride mixture. Catalyst life may be extended if carbon disulfide is present in the feed stream. The addition of water to the feed enhances selectivity towards olefins and a yield of ethylene of over 60 wt % is reported when a mixture of 36% methanol, 64% water and 2000 ppm of carbon disulfide is passed over the catalyst.

U.S. Pat. No. 3,911,041 and Kaeding et al., J. Catalysis 61, 155 (1980), disclose the conversion of methanol to olefins, with up to 70% selectivity to $C_2$–$C_4$ olefins at 100% conversion over a crystalline aluminosilicate zeolite having a silica to alumina ratio of at least about 12, a constraint index of about 1 to 12, features demonstrated by ZSM-5, ZSM-11, ZSM-12, ZSM-21 and TEA mordenite, and having at least about 0.78 wt % phosphorus incorporated with the crystal structure.

It is an object of this invention to provide a catalytic process for converting methanol and/or dimethyl ether to hydrocarbons which are rich in light monoolefins, especially ethylene and propylene, in high yields and at high conversions. Another object is to provide such a process wherein the catalyst is effective in the formation of light monoolefins as soon as it is contacted with the feed stream, that is, without a substantial induction period. Still another object is to provide such a process which employs as the catalyst an aluminosilicate which need not have a silica to alumina ratio of at least about 12 and which need not have a pore size of less than 6 A (0.6 nm) in the major dimension. A further object is to produce light monoolefins by a process which is not dependent on crude oil as a source material. Other objects will become apparent hereinafter.

DISCLOSURE OF THE INVENTION

For further comprehension of the invention, and of the objects and advantages thereof, reference may be made to the following description and to the appended claims in which the various novel features of the invention are more particularly set forth.

The invention herein resides in the process of preparing hydrocarbons rich in light monoolefins by:

(a) activating a hydrogen-exchanged aluminosilicate catalyst having a silica to alumina ratio of less than 12 and, optionally, containing added metal cations, by treating with steam at a temperature of at least 400° C., preferably 450° to 520° C.;

(b) contacting the steam-activated catalyst in a reaction zone, at a temperature of about 350° to about 600° C., preferably 450° to 520° C., with a gas stream consisting essentially of dimethyl ether or a mixture of methanol and dimethyl ether, as reactant, and sufficient water such that the mole ratio of water to ether in the reaction zone is at least 0.3, at a pressure of about 0.2 to about 30 atmospheres (about 20 to about 3000 kPa), preferably atmospheric pressure (100 kPa), and at a weight hourly space velocity (WHSV) of greater than about 0.5 $h^{-1}$, preferably 1 to 150 $h^{-1}$, to convert at least 85 wt % of the reactant to hydrocarbons comprising at least 50 wt % ethylene and propylene, said 85% conversion being achieved before the contacting has exceeded 1 g of reactant per g of catalyst, preferably before exceeding 0.3 g of reactant per g of catalyst, more preferably before exceeding 0.1 g of reactant per g of catalyst, until the catalyst is spent; and (c) regenerating the spent catalyst with a mixture comprising steam and oxygen at a temperature of at least 400° C., preferably 450° to 520° C.

The term "consisting essentially of" is used in the recitation of the composition of the gas stream to show the essential components thereof, that is, the ether or mixture of alcohol and ether, and water. Use of the term is not intended to preclude the presence of one or more nonessential materials in the gas stream, for example, an inert carrier gas, provided such material does not substantially adversely affect the process of the invention. "Light monoolefins", as the term is used herein, is intended to encompass primarily monoolefins of 2 to 4 carbon atoms, especially ethylene and propylene.

It is to be understood that, in the practice of this invention, materials present in the feed stream to the reaction zone may consist of methanol, dimethyl ether, or a mixture thereof. However, under the reaction zone process conditions recited above, methanol, upon entering the reaction zone, is converted to dimethyl ether and water. More specifically, one mole of methanol can provide 0.5 mole of ether and 0.5 mole of water. Thus, when only methanol is present in the feed stream to the reaction zone, dimethyl ether and water are produced in the reaction zone. The resultant gas stream consists essentially of dimethyl ether or a mixture of methanol and dimethyl ether and sufficient water, produced in situ, such that the mole ratio of water to ether exceeds the required minimum of 0.3. Addition of water to a feed stream containing only methanol is, therefore, not essential. It is to be further understood, in light of the above discussion, that the invention is intended to include any process wherein the feed stream entering the reaction zone may consist essentially of only methanol, yielding in the reaction zone a gas stream consisting essentially of dimethyl ether or a mixture of methanol and dimethyl ether.

In preferred embodiments of the process of the invention, at least 85% conversion of reactant to hydrocarbons is achieved before said contacting has exceecded 0.3 g of reactant per g of catalyst, and still more preferably, before said contacting has exceeded 0.1 g of reactant per g of catalyst. In other preferred embodiments wherein the catalyst is regenerated a plurality of times, the catalyst life is in excess of eighty hours and, at 100% conversion of reactant, the resultant hydrocarbons contain at least 75%, for example, 77 to 83%, ethylene and propylene, of which monoolefins at least 50%, for example, 50 to 70%, is ethylene.

It is important that the reactant and water be thoroughly mixed prior to the contacting of the catalyst by the gas stream in the reaction zone. As already suggested, an inert gas, such as nitrogen, hydrogen or helium, can be employed to carry the reactant charge through the catalyst zone, and/or to adjust WHSV.

Aluminosilicates which are useful in the process of this invention include crystalline and amorphous aluminosilicates, the former being preferred. Zeolites, which are the preferred crystalline aluminosilicates herein, include, but are not limited to, naturally-occurring chabazites which appear to contain about 60 wt % chabazite, the remainder being largely erionite. Useful naturally occurring chabazites include Norton Zeolon ® 500 and Union Carbide AW500. Also useful are Durke-Oregon chabazite-erionite and Christmas-Arizona chabazite-quartz-sanidine which are richer in chabazite. Erionite, and related structures, and mordenite, both natural and synthetic are also useful. Several aluminosilicate minerals, particularly the chabazites, are catalytically active as mined for converting the reactant to hydrocarbons, that is, without hydrogen-exchange treatment, but significantly improved activity is obtained by replacing the major portion of alkali or alkaline earth metals originally present with hydrogen ions. Procedures for carrying out the hydrogen-exchange are well known and are included, for example, in U.S. Pat. Nos. 4,062,905; 4,075,095; and 4,075,096.

Aluminosilicates which are useful in the process of this invention may also contain cations of various metals, such as those of strontium and barium, the metal cations also being introduced by known ion-exchange methods, for example, by cation exchange of the aluminosilicate in its hydrogen form. Operable aluminosilicates can have large or small pores provided that the molar silica to alumina ratio is less than 12.

As is well known in the art zeolitic catalysts lose their activity for converting methanol and/or dimethyl ether to olefin-rich hydrocarbons. Such loss of activity, which is characterized by a decrease in conversion of reactant to hydrocarbons, depends on a variety of factors, including catalyst type and process, temperature, WHSV and pressure, and is signalled by a decrease in conversion of reactant to hydrocarbons; selectivity to olefins is usually relatively little affected by this activity loss when water is present. Loss in activity is believed to result from excessive depostion of carbon on the catalyst (coking). Deactivated catalysts conventionally are regenerated by heating at relatively high temperatures in air or oxygen.

Art aluminosilicate catalysts are generally conventionally calcined (activated) in air prior to use. The aluminosilicate catalyst used in the process of this invention must be activated prior to use by heating in an atmosphere comprising steam and, optionally, oxygen or air, at a temperature of at least 400° C., preferably 450° to 520° C., most preferably at the reactant conversion temperature employed in the process. When the catalyst is spent, that is, when the conversion of reactant to hydrocarbons falls significantly below 85%, it must be regenerated by heating in an atmosphere of steam admixed with oxygen or air, at a temperature of at least 400° C., preferably 450° to 520° C., most preferably at the reactant conversion temperature. Such activation and/or regeneration must be carried out for such a time that the resultant catalyst is effective in converting at least 85% of the reactant to hydrocarbons, of which at least 50 wt % is ethylene and propylene, before the reactant in the feed stream contacting the catalyst has exceeded 1 g per g of catalyst, preferably before exceeding 0.3 g of reactant per g of catalyst, more preferably before exceeding 0.1 g of reactant per g of catalyst. The time required for catalyst activation or regeneration depends on a variety of factors such as catalyst type, temperature, and steam to oxygen ratio; it can vary from about 10 minutes to several hours. Generally, about 30 minutes is sufficient. The steam to oxygen ratio, by gaseous volume, can be about 0.2 to about 100, preferably 1 to 10. It is preferable to maintain the activated catalyst under pure steam at all times other than during reaction or regeneration cycles.

In practicing the process of this invention, the gas stream and activated catalyst are contacted in a suitable reaction zone, for example, in a fixed bed of catalyst, under effective conversion conditions, sometimes hereinafter referred to as reaction conditions. Such conditions include an operating temperature of about 350° to about 600° C., preferably 450° to 520° C., a total pressure of about 0.2 to about 30 atmospheres (about 20 to about 3000 kPa), preferably atmospheric pressure, and a weight hourly space velocity (WHSV) of greater than about $0.5\ h^{-1}$, preferably 1 to $150\ h^{-1}$. The process can be carried out in a continuous or semi-continuous mode of operation. In one preferred embodiment, a pre-mixed charge of reactant and water is passed, in vapor form, through a fixed bed of granulated activated catalyst maintained at the reaction temperature. Alternatively, the activated catalyst particles can be moving, for example, fluidized, and the gas stream passed concurrently or countercurrently through the activated catalyst.

It also has been found convenient to operate the process of the invention in a cyclic mode wherein in each cycle the catalyst, after steam-activation, is exposed to the gas stream for a suitable reaction period, for example, 1 to 20 minutes, then steam-air for a suitable regeneration period, for example, 20 to 60 minutes. Exit gases are normally sampled and analyzed at the end of the product formation cycle. Cyclic operation has been demonstrated in the manner indicated with a single catalyst sample (hydrogen-exchanged Norton Zeolon ® 500) for over 240 reaction-regeneration cycles, each cycle being carried out at 100% conversion of reactant to hydrocarbons, the product containing 77-83 wt % of ethylene and propylene, of which 50 to 70% was ethylene. Data are shown in Table 1. Regeneration was effected with steam/air at the reactant conversion temperature; equal times were used for the conversion and regeneration cycles; the ratio of air to steam was 1:1 by gaseous volume. The last column in Table 1 shows the total hours (cumulative) in the reaction cycles.

TABLE 1

| Feed | Reaction Temperature (°C.) | Yield (%) Ethylene | Yield (%) Ethylene + Propylene | Hours in Reaction Cycle |
| --- | --- | --- | --- | --- |
| DME | 460 | 46 | 83 | 0-45 |
| DME | 550 | 56 | 80 | 45-52 |
| CH₃OH | 550 | 51 | 77 | 52-57 |
| CH₃OH | 500 | 48 | 81 | 57-71 |
| CH₃OH | 460 | 40 | 80 | 72-77 |
| CH₃OH | 550 | 51 | 77 | 77-80 |

Continuous (uninterrupted) conversion of reactant to hydrocarbons can be achieved by operating with two or more catalyst beds in parallel, one or more in the reaction mode, the other(s) in the regeneration mode.

The hydrocarbons produced consist very largely of hydrocarbons rich in light monoolefins and containing less than five carbon atoms. Exit gases include water and, when conversions are less than 100%, small quantities of reactant.

Specific embodiments of this invention are provided in the following examples. It is to be understood that not all of the examples are within the invention. Those outside the invention are provided for comparison. Percentages are by weight and temperatures are in degrees Celcius, unless otherwise indicated. Conversions are based on the amount of reactant carbon which is converted to hydrocarbons.

EXAMPLE 1–9

The first eight of these examples were carried out using dimethyl ether as the reactant, the ninth, using methanol as the reactant. In all examples chabazite was used as the catalyst. The letters used in the second column of Table 2 to designate the catalyst mean the following:

A: Norton Zeolon ® 500, $Sr^{2+}$-exch.
B: Union Carbide AW500, as received
C: Norton Zeolon ® 500, as received
D: Union Carbide AW500, $NH_4^+$-exch., calcined
E: Norton Zeolon ® 500, $NH_4^+$-exch., calcined
F: Christmas-Arizona, $NH_4^+$-exch., calcined
G: Durke-Oregon, $NH_4^+$-exch., calcined Table 2 also provides additional data for Examples 1 to 9 which are described in greater detail below.

EXAMPLES 1 and 2

Chabazite catalyst in the form of 20-40 mesh (U.S. Sieve Series) particles, occupying a volume of 2.0 cc (approximately 1.0 g) was placed in a Pyrex ® U-tube reactor immersed in a fluidized, heated sand bath. Water was fed to the reactor by means of an automatic flow pump. The catalyst was heated to the desired reaction temperature under steam. Dimethyl ether was then admixed with water, in desired proportions, by means of a mixing T, and the reactant/water mixture was fed to the catalyst bed for 5 to 20 minutes as required to reach steady state conditions. At the end of this period the exit gases were split into two streams for analytical purposes. The first sample was fed through a column containing 0.61 m of Porapak ® Q and 3 m of 10% Carbowax ® on Chromasorb ® 101. $C_1$–$C_4$ hydrocarbon products and oxygenated molecules were separated quantitatively on this column. The second gas sample was fed to a 3 m column containing 10% Carbowax ® on Chromasorb ® 101 which separates $C_5$–$C_{10}$ hydrocarbons contained in the product gas.

EXAMPLES 3 to 9

For these examples, the reactor containing 1.0 g (about 2.0 cc) of chabazite was operated in the following cyclic manner. The catalyst was heated to reaction temperature under steam and then contacted with a mixture of reactant (methanol or dimethyl ether) and water for 20 minutes. The catalyst was then returned to a water-only atmosphere for 5 minutes, then air (113 cc/min) and water for 20 minutes, a further 5 minutes under water, and then reactant/water (reaction cycle) again for 20 minutes. Catalyst (reaction) temperature was changed, if desired, during the water-only mode. Exit gases were collected and analyzed, as described for Examples 1 and 2, at the end of each 20-minute reaction cycle.

TABLE 2

| Ex. | Catalyst | Reactant Flow Rate (g/h) | Water Flow Rate (g/h) | Water (mol %) | Reaction Temp. (°C.) | Contact Time (sec) | WHSV (h$^{-1}$) | Conversion (wt %) | Hydrocarbon Selectivity (wt %) | | | | | | |
|---|---|---|---|---|---|---|---|---|---|---|---|---|---|---|---|
| | | | | | | | | | CH$_4$ | C$_2$H$_4$ | C$_2$H$_6$ | C$_3$H$_6$ | C$_3$H$_8$ | C$_4$+ | C$_2$H$_4$ + C$_3$H$_6$ |
| 1 | A | 3.6 | 5.0 | 78 | 550 | 0.30 | 8.6 | 100 | 15 | 62 | 1 | 19 | — | 4 | 81 |
| 2 | B | 3.6 | 5.0 | 78 | 500 | 0.32 | 8.6 | 42 | 20 | 41 | 1 | 32 | — | 7 | 73 |
| 3 | C | 3.6 | 5.0 | 78 | 460 | 0.34 | 8.6 | 83 | 2 | 46 | 2 | 41 | 1 | 7 | 87 |
| 4 | C | 8.2 | 3.2 | 50 | 460 | 0.34 | 11.4 | 64 | 2 | 41 | 2 | 45 | 1 | 9 | 86 |
| 5 | D | 3.6 | 5.0 | 78 | 460 | 0.34 | 8.6 | 96 | 3 | 47 | 1 | 33 | 6 | 10 | 80 |
| 6 | E | 3.6 | 5.0 | 78 | 460 | 0.34 | 8.6 | 60 | 4 | 52 | 2 | 31 | 4 | 7 | 83 |
| 7 | F | 3.6 | 5.0 | 78 | 460 | 0.34 | 8.6 | 100 | 1 | 50 | 1 | 38 | 5 | 6 | 88 |
| 8 | G | 3.6 | 5.0 | 78 | 500 | 0.32 | 8.6 | 100 | 5 | 44 | 7 | 7 | 28 | 7 | 72 |
| 9 | C | 5.1 | 3.8 | 57 | 500 | 0.31 | 8.9 | 100 | — | 48 | — | — | 33 | — | 81 |

EXAMPLES 10 to 21

All of these examples were carried out using dimethyl ether as the reactant. The catalysts employed were hydrogen-exchanged: natural chabazite (Examples 10 to 15); erionite (Examples 16 to 18); and mordenite (Examples 19 to 21). Tables 3 to 5 provide additional data for Examples 10 to 21 which are described in greater detail below. It is to be understood that, for reasons given hereinafter, Examples 10, 11, 14, 15 and 17, a portion of Part D of Example 20, and Example 21 are not within the process of the invention.

EXAMPLE 10

A. Using the reactor arrangement described for Examples 3 to 9, 1 g of hydrogen-exchanged natural chabazite (Catalyst C of Table 2) was heated in air to 485°, then exposed to a 1:1 (by volume; 1:3.5 molar) mixture of dimethyl ether (DME) and water (10 ml/h total) for 1 minute, at the end of which period the exit gases were sampled and analyzed by gas chromatography. The catalyst was re-exposed to air at 485° for approximately 1 hour, and DME/H$_2$O was reintroduced for 6 minutes, followed by exit gas analysis. Further introductions of DME/H$_2$O were made for periods of 11, 21, and 31 minutes, respectively, the catalyst being exposed to air at the reaction temperature prior to each such reaction period. Exit gases were analyzed at the end of each reaction period with the results shown in Table 3.

B. The procedure of Part A was repeated to the extent that the fresh catalyst sample was heated to 485° under helium instead of air and then exposed to 1:1 DME/H$_2$O for 1 minute followed by exit gas analysis. Results are given in Table 3.

EXAMPLE 11

The catalyst used in Example 10A was heated in air at 485° C. for approximately 1 hour, after which the cyclic DME-H$_2$O/air procedure described in Example 10A was repeated; reaction periods of 1, 6, 11, 21, and 31 minutes were each preceded by a 1 hour exposure to air at 485°. Results are given in Table 3.

EXAMPLE 12

A fresh 1 g sample of catalyst C of Table 2 (see Example 10A) was exposed to steam (5 ml/h H$_2$O) for 18 hours, then to 1:1 (by volume; 1:3.5 molar) DME-H$_2$O for periods of 1 minute, 5 minutes, 5 minutes, 10 minutes and 10 minutes, totalling 31 minutes. Between each period the catalyst was exposed to steam only, at 485° C., for approximately 1 hour. Exit gases were sampled and analyzed after each reaction period. Results are given in Table 3.

EXAMPLE 13

The catalyst used in Example 12 was regenerated by exposure to a 1:1 (by volume; 1:3.5 molar) mixture of air and steam at 485° C. for approximately 1 hour, then subjected to the cyclic DME-H$_2$O/H$_2$O procedure described in Example 12. Results are given in Table 3.

EXAMPLE 14

A fresh 1 g sample of catalyst C of Table 2 (see Example 10A) was heated in nitrogen to 485°, then exposed to a 1:3.5 molar mixture of DME and nitrogen for periods of 2, 6, 11 and 21 minutes, between each such period the catalyst being exposed to nitrogen at the reaction temperature. Exit gases were analyzed at the end of each reaction period. Results are given in Table 3.

EXAMPLE 15

The catalyst used in Example 14 was heated at 485° C. in a 1:1 (by volume) mixture of nitrogen and air for approximately 1 hour, and then subjected to the cyclic DME-N$_2$/N$_2$ procedure similar to that described in Example 14, with reaction periods of 1, 6, 11, 16 and 21 minute duration. The results are given in Table 3.

TABLE 3

| Ex. | Reaction Time (min) | g DME / g catalyst | Conversion (wt %) | Hydrocarbon Selectivity (wt %) | |
|---|---|---|---|---|---|
| | | | | C$_2$H$_4$ | C$_2$H$_4$ + C$_3$H$_6$ |
| 10A | 1 | 0.06 | 100 | 17 | 17 |
| | 6 | 0.36 | 100 | 30 | 57 |
| | 11 | 0.66 | 100 | 41 | 72 |
| | 21 | 1.27 | 100 | 52 | 85 |
| | 31 | 1.87 | 14 | 51 | 76 |
| 10B | 1 | 0.06 | 100 | 11 | 11 |
| | | | | (Propane, 65%) | |
| 11 | 1 | 0.06 | 100 | 21 | 21 |
| | 6 | 0.36 | 100 | 33 | 62 |
| | 11 | 0.66 | 100 | 40 | 71 |
| | 21 | 1.27 | 100 | 50 | 82 |
| | 31 | 1.87 | 27 | 57 | 82 |
| 12 | 1 | 0.06 | 100 | 36 | 58 |
| | 5 | 0.30 | 100 | 39 | 72 |
| | 5 | 0.30 | 100 | 43 | 75 |
| | 10 | 0.60 | 100 | 48 | 79 |
| | 10 | 0.60 | 59 | 53 | 84 |
| 13 | 1 | 0.06 | 100 | 32 | 64 |
| | 5 | 0.30 | 100 | 40 | 70 |
| | 5 | 0.30 | 100 | 44 | 71 |
| | 10 | 0.60 | 100 | 49 | 82 |
| | 10 | 0.60 | 42 | 55 | 80 |
| 14 | 2 | 0.12 | 100 | 9 | 10 |
| | | | | (Propane, 65%) | |
| | 6 | 0.36 | 100 | 11 | 22 |
| | | | | (Propane, 52%) | |
| | 11 | 0.66 | 100 | 19 | 46 |
| | 21 | 1.27 | 8 | 38 | 55 |
| 15 | 1 | 0.06 | 100 | 10 | 17 |

TABLE 3-continued

| Ex. | Reaction Time (min) | g DME / g catalyst | Conversion (wt %) | Hydrocarbon Selectivity (wt %) | |
|---|---|---|---|---|---|
| | | | | $C_2H_4$ | $C_2H_4 + C_3H_6$ |
| | 6 | 0.36 | 100 | 13 | 27 (Propane, 57%) |
| | 11 | 0.66 | 100 | 27 | 60 (Propane, 43%) |
| | 16 | 0.96 | 69 | 52 | 82 |
| | 21 | 1.27 | 9 | 43 | 62 |

Examples 10, 11, 14 and 15, which are outside the invention, show that the art procedures of catalyst activation in an inert gas such as He or $N_2$, or catalyst regeneration in air only, while effective in rapidly restoring reactant conversion to hydrocarbons, are comparatively slow in restoring selectivity to the formation of ethylene and propylene. Comparison of Examples 10A, 10B or 14 with Example 12 shows the effect of activation in air, He or $N_2$ and in steam; the latter (Example 12) results in 58% selectivity after 0.06 g DME/g catalyst exposure; the former (Examples 10A, 10B, 14) result in 17%, 11% and less than 10% selectivity, respectively, after the same exposure.

Similarly, a comparison of Examples 11 and 15 with Example 13 shows that 0.06 g DME/g catalyst exposure results in a 17–21% selectivity for air-regenerated catalyst, and a 64% selectivity for catalyst regenerated by the air/steam procedure of this invention. Examples 14 and 15 also indicate that selectivity to lower olefins is further retarded when water in the feed stream is replaced by nitrogen.

EXAMPLE 16

Using the experimental arrangement of Examples 3 to 9, a 1 g sample of previously used hydrogen-exchanged erionite was regenerated in a 1:1 mixture of air and steam at 464° for 1.1 hours, then contacted with a 1:1 DME/$H_2O$ (10 ml/h total) mixture for 10 minutes, followed by exit gas analysis. Results are given in Table 5.

EXAMPLE 17

The catalyst used in Example 16 was heated in air only at 480° for 17 hours, then exposed to 1:1 DME/$H_2O$ as in Example 16 for 10 minutes, followed approximately 1 hour later by a further 30 minute exposure to 1:1 DME/$H_2O$. The catalyst was exposed to steam at 480° C. between reaction periods. Exit gases were analyzed after each period, with the following results:

TABLE 4

| Reaction Time (min) | g DME / g catalyst | Conversion (wt %) | Hydrocarbon Selectivity (wt %) | |
|---|---|---|---|---|
| | | | $C_2H_4$ | $C_2H_4 + C_3H_6$ |
| 10 | 0.60 | 100 | 17 | 33 |

TABLE 4-continued

| Reaction Time (min) | g DME / g catalyst | Conversion (wt %) | Hydrocarbon Selectivity (wt %) | |
|---|---|---|---|---|
| | | | $C_2H_4$ | $C_2H_4 + C_3H_6$ |
| 30 | 1.80 | 7 | 48 | 62 |

EXAMPLE 18

The catalyst used in Example 17 was regenerated in 1:1 air/steam for 1 hour at 480°, then contacted with 1:1 DME/$H_2O$ as in Example 16 for 10 minutes, followed by exit gas analysis. Results are given in Table 5. Example 17, which is outside this invention, illustrates that regeneration in air only is effective in restoring or maintaining erionite catalyst activity (% conversion) but is detrimental to olefin selectivity in the earlier stages of reaction. Example 18 shows that regeneration of the catalyst in steam and air restores catalyst activity without loss of olefin selectivity.

TABLE 5

| Ex. | Reaction Time (min) | g DME / g catalyst | Conversion (wt %) | Hydrocarbon Selectivity (wt %) | | | | | | |
|---|---|---|---|---|---|---|---|---|---|---|
| | | | | $CH_4$ | $C_2H_4$ | $C_2H_6$ | $C_3H_6$ | $C_3H_8$ | $C_4^+$ | $C_2H_4 + C_3H_6$ |
| 16 | 10 | 0.60 | 100 | 4 | 62 | 3 | 23 | 5 | 4 | 85 |
| 18 | 10 | 0.60 | 99 | 7 | 66 | 3 | 18 | 4 | 2 | 84 |

EXAMPLE 19

Using the reactor arrangement described for Examples 3 to 9, 1 g of hydrogen-exchanged natural mordenite was heated to 470° in an atmosphere of water vapor (5 ml of liquid water per hour) and conditioned by exposure to these conditions for 18 hours. A 1:1 (by volume) mixture of dimethyl ether (DME) and water (10 ml/h total) was then passed over the steam-exposed catalyst for 1 minute, after which a sample of the exit stream was collected and analyzed by gas chromatography as previously described. Results are given in Table 6.

EXAMPLE 20

A. The experiment of Example 19 was repeated except that a fresh H+ mordenite catalyst was conditioned by heating for 18.5 hours at 468° under steam and the exit gases were sampled after 10 minutes exposure to 1:1 DME/$H_2O$ (10 ml/h). Results are given in Table 6.

B. The catalyst used in Part A was further contacted with 1:1 DME/$H_2O$ at 472° until the conversion had decreased to 50%; selectivities to ethylene and propylene totalled 82% (62% E, 20% P). The catalyst was then regenerated in air/$H_2O$ (0.15:1) at 427° for 18.5 hours, followed by exposure to 1:1 DME/$H_2O$ (10 ml/h total) for 10 minutes. Results are given in Table 6.

C. The catalyst used in Part B was further contacted with DME/$H_2O$ at 482° until conversion had declined to 54%; selectivities to ethylene and propylene totalled 87% (57% E, 30% P). The catalyst was then regenerated in air/$H_2O$ (0.15:1) at 482° for 30 minutes, followed by exposure to 1:1 DME/$H_2O$ (10 ml/h total) for 1 minute (0.06 g DME/g catalyst). Exit gas analysis showed: conversion, 100 wt %; selectivity to ethylene and propylene, 77% (49% E, 28% P).

D. The catalyst used in Part C was further contacted with DME/$H_2O$ at 482° until conversion had declined to 36%; selectivities to ethylene and propylene totalled 81% (64% E, 17% P). The catalyst was then exposed to steam only at 470° for 67 hours, followed by 1:1 DME/H₂O (10 ml/h total) for 1 minute (0.06 g DME/g catalyst). Exit gas analysis showed that although selectivity to ethylene and propylene was 82% (55% E, 27% P), conversion was only 61 wt %, indicating the inadequacy of steam for catalyst regeneration. The catalyst was then exposed to air/H₂O (0.15:1) at 482° for 1 hour, followed by 1:1 DME/H₂O for 1 minute. Exit gas analysis showed: conversion, 100 wt %; selectivity to ethylene and propylene, 71% (39% E, 32% P).

EXAMPLE 21

A. Fresh 1 g sample of hydrogen-exchanged mordenite, similar to that used in Examples 19 and 20, was heated in air (113 cc/min) at 462° for 17.5 hours and then exposed to 1:1 DME/H₂O (10 ml/h total) for 1 minute. Exit gas analysis gave the results shown in Table 6; selectivity to ethylene and propylene totalled only 5 wt. %.

B. The catalyst used in Part A was further contacted with DME/H₂O until conversion had declined to 22%; selectivity to ethylene and propylene had risen to 71% (44% E, 27% P). The catalyst was then reheated in air at 466° for 1.1 hours, then reexposed to 1:1 DME/H₂O for 1 minute. Exit gases were sampled and analyzed with the results shown in Table 6. Air treatment had clearly restored catalyst activity, but the major product was propane, not the desired olefins.

TABLE 6

| Ex. | Reaction Time (min) | g DME / g catalyst | Conversion (wt %) | Hydrocarbon Selectivity (wt %) | | | | | | |
|---|---|---|---|---|---|---|---|---|---|---|
| | | | | $CH_4$ | $C_2H_4$ | $C_2H_6$ | $C_3H_6$ | $C_3H_8$ | $C_4^+$ | $C_2H_4 + C_3H_6$ |
| 19 | 1 | 0.06 | 100 | 2 | 30 | 3 | 34 | 17 | 15 | 64 |
| 20A | 10 | 0.60 | 100 | 3 | 39 | 3 | 38 | 4 | 13 | 77 |
| 20B | 10 | 0.60 | 100 | 3 | 29 | 4 | 32 | 18 | 14 | 61 |
| 21A | 1 | 0.06 | 100 | 11 | 5 | 19 | 0 | 59 | 7 | 5 |
| 21B | 1 | 0.06 | 100 | 12 | 5 | 20 | 4 | 53 | 6 | 9 |

BEST MODE FOR CARRYING OUT THE INVENTION

The best mode presently contemplated for carrying out the invention resides in the cyclic procedure described just before the examples, with the results shown in Table 1.

INDUSTRIAL APPLICABILITY

Industrial uses for the ethylene and propylene prepared by the process of this invention are well known in the art and need not be recited here.

Although the preferred embodiments have been illustrated and described above, it is to be understood that it is not intended to limit the invention to the precise constructions herein disclosed and it is to be further understood that the right is reserved to all changes and modifications coming within the scope of the invention as defined in the appended claims.

I claim:

1. Process of preparing hydrocarbons rich in light monoolefins by:
    (a) activating a hydrogen-exchanged aluminosilicate catalyst having a silica to alumina ratio of less than 12 by treating with steam at a temperature of at least 400° C.;
    (b) contacting the steam-activated catalyst in a reaction zone, at a temperature of about 350° to about 600° C., with a gas stream consisting essentially of dimethyl ether or a mixture of methanol and dimethyl ether, as reactant, and sufficient water such that the mole ratio of water to ether in the reaction zone is at least 0.3, at a pressure of about 0.2 to about 30 atmospheres (about 20 to about 3000 kPa), and at a weight hourly space velocity (WHSV) of greater than about 0.5 h⁻¹, to convert at least 85 wt % of the reactant to hydrocarbons comprising at least 50 wt % ethylene and propylene, said 85% conversion being achieved before the contacting has exceeded 1 g of reactant per g of catalyst, until the catalyst is spent; and
    (c) regenerating the spent catalyst with a mixture comprising steam and oxygen at a temperature of at least 400° C.

2. Process of claim 1 wherein the 85% conversion is achieved before the contacting has exceeded 0.3 g of reactant per g of catalyst.

3. Process of claim 1 wherein the 85% conversion is achieved before the contacting has exceeded 0.1 g of reactant per g of catalyst.

4. Process of claim 1 wherein steps (b) and (c) are repeated a plurality of times.

5. Process of claim 2 wherein the catalyst includes added metal cations.

6. Process of claim 3 wherein the catalyst includes added metal cations.

7. Process of claim 1 wherein air is used to provide the oxygen in step (c).

8. Process of claim 1 wherein the conversion of reactant into hydrocarbons is 100% and the hydrocarbons contain at least 75 wt % of the monoolefins ethylene and propylene, of which monoolefins at least 50% is ethylene.

9. Process of claim 1 wherein the contacting in step (b) is carried out at 450° to 520° C., the catalyst activation and catalyst regeneration temperatures in steps (a) and (c) are 450° to 520° C., the pressure is about atmospheric pressure (about 100 kPa), and the WHSV is 1 to 150 h⁻¹.

10. Process of claim 9 wherein the catalyst includes added metal cations.

11. Process of claim 10 wherein the added metal cation is a cation of barium or strontium.

12. Process of claim 1 which is carried out in a continuous mode of operation.

13. Process of claim 1 which is carried out in a semicontinuous mode of operation.

14. Process of claim 1 wherein the catalyst is a crystalline aluminosilicate.

15. Process of claim 14 wherein the crystalline aluminosilicate is a zeolite.

* * * * *